US 6,437,358 B1

(12) United States Patent
Potucek et al.

(10) Patent No.: US 6,437,358 B1
(45) Date of Patent: Aug. 20, 2002

(54) APPARATUS AND METHODS FOR CAPTURING DEFECT DATA

(75) Inventors: Martin Potucek; Albert D. Edgar; Darryl R. Polk, all of Austin, TX (US)

(73) Assignee: Applied Science Fiction, Inc., Austin, TX (US)

( * ) Notice: Subject to any disclaimer, the term of this patent is extended or adjusted under 35 U.S.C. 154(b) by 0 days.

(21) Appl. No.: 09/244,196

(22) Filed: Feb. 4, 1999

(51) Int. Cl.$^7$ .............................................. G01N 21/86
(52) U.S. Cl. ........................... 250/559.45; 250/559.07; 250/559.11; 382/275
(58) Field of Search ....................... 250/559.01, 559.02, 250/559.05, 559.07, 559.11, 559.4, 559.41, 559.44, 559.45, 559.48, 548, 216, 284, 208.1; 355/53, 67, 71; 356/237.1, 237.2, 239.1, 239.7, 239.8; 382/108, 112, 149, 254, 275

(56) References Cited

U.S. PATENT DOCUMENTS

| 4,260,899 A | 4/1981 | Baker ........................... 250/562 |
| 4,301,469 A | 11/1981 | Modeen et al. ............... 358/75 |

(List continued on next page.)

FOREIGN PATENT DOCUMENTS

| EP | 0 482 790 B1 | 4/1992 | ............. H04N/1/40 |
| EP | 0 716 538 A2 | 6/1996 | ............. H04N/1/50 |
| EP | 0 751 670 A | 1/1997 | ............. H04N/1/10 |
| EP | 0 768 621 A2 | 4/1997 | ............. G06T/5/20 |
| EP | 0 794 454 A2 | 9/1997 | ............ G03B/27/73 |
| EP | 0 816 833 A2 | 1/1998 | ........... G01N/21/88 |
| EP | 0 816 833 A3 | 8/1998 | ........... G01N/21/88 |
| EP | 0 893 914 A2 | 1/1999 | ........... H04N/5/253 |
| JP | 4-291139 A | * 10/1992 | ............. 250/559.45 |
| JP | 11185028 | 7/1999 | ............. G06T/1/00 |
| JP | 2000-13604 | 1/2000 | ........... H04N/1/409 |
| JP | 2000-196813 A | 7/2000 | |
| WO | 28 21 868 A1 | 5/1979 | ........... G01N/21/32 |
| WO | 1 5 47 811 | 6/1979 | ............. H04N/3/36 |
| WO | WO 84/02019 | 5/1984 | ............ G06F/15/20 |
| WO | WO 89/06890 | 7/1989 | ............. H04N/3/36 |
| WO | WO 90/01240 | 2/1990 | ............. H04N/1/40 |
| WO | 0 422 220 A1 | 4/1991 | ............. A61B/6/03 |
| WO | WO 91/09493 | 6/1991 | ........... H04N/5/217 |
| WO | WO 92/05469 | 4/1992 | ........... G03B/27/53 |

(List continued on next page.)

OTHER PUBLICATIONS

*Grayscale Characteristics*, Photographic Negatives The Nature of Color Images, Digital Color Management, Giorgianni, et al., Jan. 1998, pp. 163–168.

(List continued on next page.)

*Primary Examiner*—Que T. Le
*Assistant Examiner*—Kevin Pyo
(74) *Attorney, Agent, or Firm*—Simon, Galasso & Frantz PLC; Raymond M. Galasso

(57) ABSTRACT

The present invention provides a system for image-capturing devices, such as scanners, to accurately identify defects in objects. The objects can be the physical images to be captured or elements of the image-capturing devices such as the platen and mirrors. The image-capturing devices can then use this defect information to remove defects from captured images. The invention teaches an advantageous arrangement of illumination and sensor elements to record defect data at an angle roughly equal to the angle at which light is directed to an object, i.e. where the angle of reflection roughly equals the angle of incidence. Light reflected from surface defects has a wider diffusion and thus a lower amplitude than light reflected from the surface of the object itself. Accordingly, this characteristic can be utilized to identify defect information. Image-capturing devices can use this defect information in software applications with mathematical algorithms to enhance captured images by removing the information that corresponds to defects.

15 Claims, 6 Drawing Sheets

U.S. PATENT DOCUMENTS

| | | | |
|---|---|---|---|
| 4,302,108 A | 11/1981 | Timson | 356/359 |
| 4,462,860 A | 7/1984 | Szmanda | 156/626 |
| 4,670,779 A | 6/1987 | Nagano | 358/75 |
| 4,677,465 A | 6/1987 | Alkofer | 358/80 |
| 4,680,638 A | 7/1987 | Childs | 358/214 |
| 4,700,229 A | 10/1987 | Herrmann et al. | 358/166 |
| 4,775,238 A | 10/1988 | Weber | 356/431 |
| 4,796,061 A | 1/1989 | Ikeda et al. | 355/73 |
| 4,845,551 A | 7/1989 | Matsumoto | 358/80 |
| 4,933,566 A * | 6/1990 | Masaaki et al. | 250/559.45 |
| 4,937,720 A | 6/1990 | Kirchberg | 363/41 |
| 4,969,045 A | 11/1990 | Haruki et al. | 358/228 |
| 4,972,091 A | 11/1990 | Cielo et al. | 250/562 |
| 4,989,973 A | 2/1991 | Noso et al. | 356/239 |
| 4,994,918 A | 2/1991 | Lingemann | 358/214 |
| 5,003,379 A | 3/1991 | Moore, Jr. et al. | 358/54 |
| 5,010,401 A | 4/1991 | Murakami et al. | 358/136 |
| 5,047,968 A | 9/1991 | Carrington et al. | 364/574 |
| 5,058,982 A | 10/1991 | Katzir | 385/33 |
| 5,091,972 A | 2/1992 | Kwon et al. | 382/54 |
| 5,097,521 A | 3/1992 | Massmann | 382/54 |
| 5,149,960 A | 9/1992 | Dunne et al. | 250/226 |
| 5,155,596 A | 10/1992 | Kurtz et al. | 358/214 |
| 5,200,817 A | 4/1993 | Birnbaum | 358/80 |
| 5,266,805 A | 11/1993 | Edgar | 250/330 |
| 5,267,030 A | 11/1993 | Giorgianni et al. | 358/527 |
| 5,291,286 A | 3/1994 | Murakami et al. | 348/469 |
| 5,311,310 A | 5/1994 | Jozawa et al. | 348/416 |
| 5,335,086 A | 8/1994 | Kitanmura | 358/431 |
| 5,371,542 A | 12/1994 | Pauli et al. | 348/262 |
| 5,447,811 A | 9/1995 | Buhr et al. | 430/20 |
| 5,448,380 A | 9/1995 | Park | 358/520 |
| 5,452,018 A | 9/1995 | Capitant et al. | 348/651 |
| 5,465,155 A | 11/1995 | Edgar | 358/500 |
| 5,465,163 A | 11/1995 | Yoshihara et al. | 358/514 |
| 5,477,345 A | 12/1995 | Tse | 358/500 |
| 5,509,086 A | 4/1996 | Edgar et al. | 382/167 |
| 5,516,608 A | 5/1996 | Hobbs et al. | 430/30 |
| 5,552,904 A | 9/1996 | Ryoo et al. | 358/518 |
| 5,561,611 A | 10/1996 | Avinash | 364/553 |
| 5,565,931 A | 10/1996 | Girod | 348/675 |
| 5,568,270 A | 10/1996 | Endo | 358/298 |
| 5,581,376 A | 12/1996 | Harrington | 358/518 |
| 5,582,961 A | 12/1996 | Giorgianni et al. | 430/508 |
| 5,583,950 A | 12/1996 | Prokoski | 382/212 |
| 5,589,887 A | 12/1996 | Wischermann | 348/616 |
| 5,608,547 A | 3/1997 | Nakatani et al. | 358/505 |
| 5,641,596 A | 6/1997 | Gray et al. | 430/21 |
| 5,666,443 A | 9/1997 | Kumashiro | 382/266 |
| 5,673,336 A | 9/1997 | Edgar et al. | 382/167 |
| 5,721,624 A | 2/1998 | Kumashiro et al. | 358/450 |
| 5,726,773 A | 3/1998 | Mehlo et al. | 358/474 |
| 5,729,631 A | 3/1998 | Wober et al. | 382/232 |
| 5,771,107 A | 6/1998 | Fujimoto et al. | 358/464 |
| 5,808,674 A | 9/1998 | Adams, Jr. et al. | 348/273 |
| 5,892,595 A | 4/1999 | Yamakawa et al. | 358/530 |
| 5,923,042 A | 7/1999 | Mietta et al. | 250/559.06 |
| 5,930,388 A | 7/1999 | Murakami et al. | 382/167 |
| 5,963,662 A | 10/1999 | Vachtsevanos et al. | 382/150 |
| 5,969,372 A | 10/1999 | Stavely et al. | 250/559.42 |
| 5,979,011 A | 11/1999 | Miyawaki et al. | 15/308 |
| 5,982,941 A | 11/1999 | Loveridge et al. | 382/260 |
| 5,982,951 A | 11/1999 | Katayama et al. | 382/284 |
| 5,991,444 A | 11/1999 | Burt et al. | 382/232 |
| 6,005,987 A | 12/1999 | Nakamura et al. | 382/294 |
| 6,057,040 A | 5/2000 | Hage | 428/447 |
| 6,075,905 A | 6/2000 | Herman et al. | 382/284 |
| 6,078,051 A * | 6/2000 | Banton et al. | 250/341.1 |
| 6,078,701 A | 6/2000 | Hsu et al. | 382/294 |
| 6,101,273 A | 8/2000 | Matama | 382/169 |
| 6,128,416 A | 10/2000 | Oura | 382/284 |
| 6,239,886 B1 | 5/2001 | Klasser et al. | 358/518 |

FOREIGN PATENT DOCUMENTS

| | | | |
|---|---|---|---|
| WO | 0 527 097 A2 | 2/1993 | H04N/1/40 |
| WO | 0 569 142 A1 | 11/1993 | H04N/5/253 |
| WO | 0 624 848 A2 | 11/1994 | G06F/15/68 |
| WO | 2 283 633 A | 5/1995 | H04N/5/262 |
| WO | WO 95/15530 | 6/1995 | G06F/17/14 |
| WO | 0 669 753 A2 | 8/1995 | H04N/1/407 |
| WO | WO 97/16028 | 5/1997 | H04N/7/30 |
| WO | 196 36 867 C1 | 1/1998 | |
| WO | WO 98/31142 | 7/1998 | H04N/5/253 |
| WO | WO 98/34397 | 8/1998 | |
| WO | WO 99/40729 | 8/1999 | H04N/9/11 |
| WO | WO 01/48694 A1 | 7/2001 | G06T/5/00 |

OTHER PUBLICATIONS

"*New Adaptive Vector Filter Based on Noise Estimate*", Mei Yu, et al., XP–000896196, IEICE Trans Fundamentals, vol. E82 A. No. 6 Jun. 1999.

"A Robust Method For Parameter Estimation of Signal–Dependent Noise Models In Digital Images", B. Aiazzi et al., Ezp–002146062, Nello Carrara Research Institute on Electromagnetic Waves IROE–CNR., pp. DSP 97–601–604, 1997.

"*A Regularized Iterative Image Restoration Algorithm*", Aggelos K. Katsaggelos, 1991.

*Adaptive Fourier Threshold Filtering: A Method to Reduce Noise and Incoherent Artifacts in High Resolution Cardiac Images*, M. Doyle et al., pp 546–550, 1994.

"Anisotropic Spectral Magnitude Estimation Filters For Noise Reduction And Image Enhancement", Til Aach et al., XP–000780652, Philips GmbH Research Laboratories, pp 335–338, 1996.

*Adaptive–neighborhood filtering of images corrupted by signal–dependent noise*, Rangaraj M. Rangayyan et al., XP–002146454, Jul. 10, 1998/ vol. 37, No. 20/ Applied Optics, pp 4477–4487.

http://www.nikonusa.com; "Digital Imaging Equipment", White Papers, Aug. 5, 1999.

"Local Cosine Transform—A Method for the Reduction of the Blocking Effect in JPEG", Journal of Mathematical Imaging and Vision, 3, 7038 (1993) ©Kluwer Academic Publishers, XP 000601160, Aharoni et al.

http://www.asf.com/html/o_products/iceprod.html; Applied Science Fiction, Digitial ICE, Aug. 5, 1999.

http://www.asf.com/html/o_products/icetech.html; Applied Science Fiction, About Digital ICE Technology, Aug. 5, 1999, pp1 and 2.

"2–D Adaptive Volterra Filter For 2–D Nonlinear Channel Equalisatioin And Image Restoration", J.–N. Lin et al., XP000280610, (1992), Electronic Letters vol. 28. No. 2.

* cited by examiner

APPARATUS AND METHODS FOR CAPTURING DEFECT DATA

FIELD OF THE INVENTION

The present invention relates generally to electronic image enhancement and recovery, and more particularly, to a method and apparatus for collecting defect data from documents and films for use in removing defects from an image.

BACKGROUND OF THE INVENTION

The field of electronic imagery has long aimed at capturing and reproducing an accurate digital representation of an image as it currently exists on a physical medium, such as a document or film. Often, however, such digital representations appear distorted. One cause of such distortions is a defect in an image-capturing system component. For example, the translucent document-scanning surface or "platen" in an electronic document image scanner might contain scratches or other optical path obstructions. More frequently, however, distortions result from factors outside the image-capturing system. For example, a photograph, film or other medium in which an image is contained might itself become scratched or otherwise distressed or deformed despite even the most careful handling. In addition, foreign matter, such as a hair or dust, might become deposited on the physical medium. Thus, even where an image captures what it "sees," distortions might yet occur.

Traditionally, the above distortions have been largely ignored in favor of increasingly accurate image capturing and reproduction. FIG. 1, for example, broadly depicts a conventional flatbed document image scanner or "flatbed scanner." (For clarity, electronic data processing and storage elements have been removed.) As shown, scanner 100 includes platen 101 and, below platen 101, light source 103, mirror 105, and sensor 107. Sensor 107 further includes lens 107a and image sensor 107b. Image sensor 107b is typically a linear or a multi-linear sensor such as a charge-coupled device ("CCD"). However, other image-capturing devices might use other sensor types. For example, a drum scanner might utilize a point or multi-point sensor, such as a photomultiplier tube or "PMT."

Operationally, an original document is positioned on platen 101 such that the source image faces platen 101. Light source 103 is then illuminated, and source image 121a is scanned. During scanning, light source 103 directs light toward and causes reflections from a region of source image 121a. Mirror assembly 105 then re-directs or "folds" the reflected light to lens 107a, which focuses received light onto image sensor 107b. Next, sensor 107b converts the focused light to electrical signals. The electrical signals are then converted to digital image data using an analog-to-digital (A/D) converter (not shown), and the digital image data is further processed and stored. While multiple sensor arrays might be utilized, the whole of image 121a is typically scanned in successive regions, thereby limiting the number of sensors needed. Such region-to-region scanning is typically accomplished by sequentially moving mirror assembly 105 and sensor 107. As mirror assembly 105 is moved, sensor 107 receives reflected light from successive regions of document 121. The image is then reconstructed from the image data during image processing.

To assure image-capturing accuracy, flatbed scanners and other optical image-capturing systems have continually refined the nature of the light source 103, mirror 105's position, and sensor 107. For example, a document, film, or other subject must be sufficiently and evenly lighted to allow capturing of image reflections from source document 121 without causing glare. Therefore, a single, typically fluorescent light source is provided. In addition, the mirror is positioned such that glare is avoided and both primarily bright and primarily dark images will be accurately captured. Therefore, each sequential mirror position is set such that light is directed from the light source to the image at a first angle and is then reflected (from the image) to a sensor at a significantly different second angle. More specifically, image clarity is assured in most devices by providing first and second angles which differ by at least 45 degrees. The resolution and optical efficiency of the sensor have also been continually improved.

Traditionally, image-capturing devices have not provided image distortion (or "defect") detection, let alone correction. Rather, their objective was strictly directed at image-capturing accuracy. Therefore, the above arrangement was considered optimal for its intended purpose. Unfortunately however, such an arrangement also produces optical effects that not only fail to provide for defect detection, but also impose an optical environment that runs counter to such an objective.

While recent image-capturing devices attempt to detect image defects, such attempts depend on the image-data accuracy provided by the above image-scanning method. In such devices, an image is scanned in the traditional manner. Scanned image data is then reviewed in much the same way that a human observer might look for defects in a reproduced image. More specifically, after capturing image data, mathematical algorithms are used to search the image data for extraneous dark spots that might be indicative of image defects. Upon locating such dark spots, the algorithms determine whether the located spots are likely indicative of an image defect, determine the graphic features of selected defects, and attempt correction. Unfortunately, defects are difficult to separate from other image data, let alone correct, by reviewing the captured image data in this manner.

A system and method that corrects defects in an image is described in U.S. Pat. No. 5,266,805, entitled "System and Method For Image Recovery", and is assigned to International Business Machines ("IBM"). The invention teaches sequentially transmitting through film red, green, blue and infrared light, and then performing correction by dividing out defects using the resulting image data, or alternatively, using an automated fill-in algorithm.

Further methods and apparatus that provides for detecting image defects are described in co-pending U.S. application Ser. No. 08/999,421, filed Dec. 29, 1997, entitled Defect Channel Nulling" and U.S. application Ser. No. 09/156,271, filed Sep. 16, 1998, entitled Method And Apparatus For Capturing Defect Data From Documents And Films, both commonly owned by the assignee of the present application.

The contents of U.S. Pat. No. 5,266,805, U.S. application Ser. Nos. 08/999,421 and 09/156,271 are hereby incorporated by reference as if repeated verbatim immediately hereinafter.

While the above prior patent and patent applications provide for defect handling in image-capturing systems, the new technological area of defect detection and correction remains subject to such a further advance as will become apparent in the discussion that follows.

Accordingly, there remains a need in the art for a system that enables defect data to be accurately captured for use in removing defects from an image.

SUMMARY OF THE INVENTION

According to a first aspect, the invention provides a positional relationship between system elements such that defects within an image are rendered more apparent. According to a second aspect, the invention provides for identifying defects within an image. According to still further aspects, the invention provides for rendering defects more apparent and identifying such defects within an image-capturing device. Advantageously, the present invention enables defects to be clearly captured, identified and corrected. In addition, the invention facilitates the use of various light sources and/or mechanisms within an image-capturing device for defect detection and/or correction in accordance with the constraints of a particular application.

The present invention provides a method and apparatus for image-capturing devices, such as scanners, to accurately identify defects in objects. The objects can be the physical images to be captured or elements of the image-capturing devices such as the platen and mirrors. The image-capturing devices can then use this defect information to remove defects from captured images.

The present invention more specifically provides a method and apparatus for recording defect data, such that light is detected at an angle roughly equal to the angle at which the light is directed to the object, i.e. where the angle of reflection roughly equals the angle of incidence. The present invention recognizes that light reflected from surface defects has a wider diffusion and thus a lower amplitude than light reflected from the surface of the object itself. The information obtained regarding the defects can be used by image-capturing devices in software applications with mathematical algorithms to enhance captured images by removing these defects.

In one embodiment, an image-capturing system preferably provides, within a flatbed scanner, light sources for image and defect scanning, a scanning controller and a defect processor. The controller regulates illumination of the light sources and movement of a conventionally provided mirror such that image information and defect data are separately captured. The image is then conventionally processed. The defect data is separately processed to identify and enable removal of defects. Preferably, reflected light is separately utilized for capturing a source image and for capturing image and system defects. During a first ("image-scanning") cycle, the controller illuminates the first light source and establishes a positional relationship among system elements for capturing the source image. During a second ("defect-scanning") cycle, the controller illuminates the second light source and establishes a positional relationship among system elements for optimally capturing defects, thereby producing defect data. Processing of the image-scan data and defect-scan data is further conducted by an image processor and defect corrector respectively in order to separately reconstruct the image and correct defects. Defect data is preferably processed in a manner corresponding to a relative intensity of captured reflected light.

In a further embodiment, a single light source is preferably utilized within a single image and defect scan cycle.

A still further embodiment provides a film scanner in which defect detection and correction are enabled in accordance with the invention.

The present invention also teaches using software to measure the maximum amplitude of the upward light wave reflected from the surface of the object at this angle. The software then calculates a threshold value for defects, based on a percentage of this maximum amplitude, and identifies as defects those areas on the object that reflect light with an amplitude at or below the threshold value.

BRIEF DESCRIPTION OF THE DRAWINGS

The above and other aspects, objects, features, and advantageous of the present invention are further described in the detailed description which follows, with reference to the drawings by way of non-limiting exemplary embodiments of the present invention, wherein like reference numerals represent similar parts of the present invention throughout several views and wherein.

DETAILED DESCRIPTION OF THE PREFERRED EMBODIMENTS

The following detailed description of the preferred embodiments will describe the present invention as it is presently preferably used with conventional flatbed scanners in order to provide defect detection and correction capability. However, it will be understood by those skilled in the art that the present invention also applies to other scanner configurations and other image-capturing devices, including but not limited to drum-type document scanners, film scanners and other image-capturing device types. Such devices might further utilize, for example, a wide variety of sensors and/or sensor components and/or sources of electromagnetic radiation (referred to hereinafter as "light sources" producing "light" or "illumination"), as is appropriate to the particular application. These and other examples will become apparent as the discussion progresses.

Figure 2:
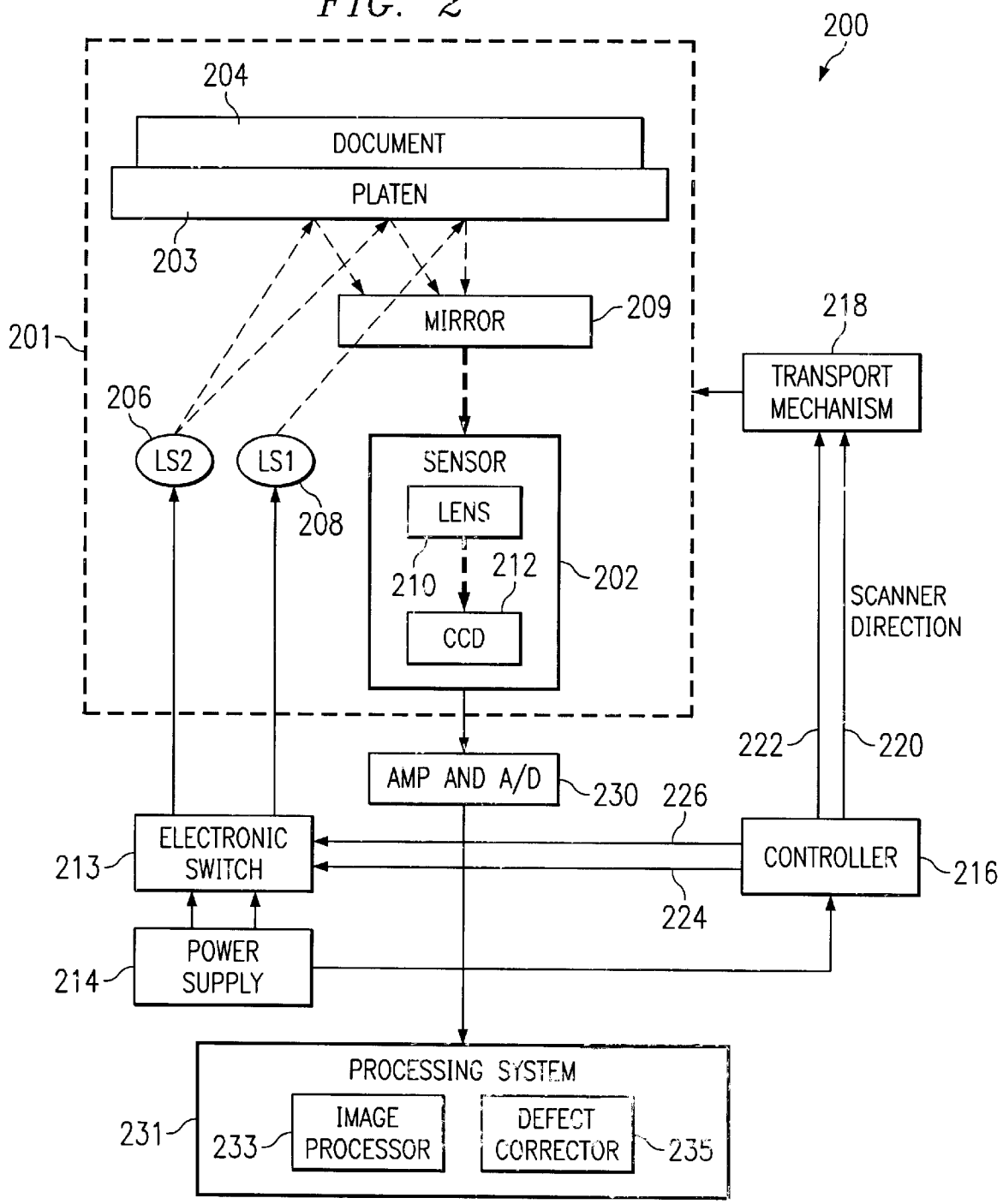
FIG. 2 illustrates an apparatus for identifying defect data in a reflective medium such as a document according to the present invention.

The FIG. 2 diagram illustrates an example of an apparatus for capturing defect data in accordance with the present invention. In this example, the defect data is captured from a reflective medium, such as a document 204. More specifically, a preferred flatbed scanner is depicted, having defect-handling capability in accordance with the present invention.

As shown in FIG. 2, system 200 comprises coupled elements including first light source (LS1) 208, second light source (LS2) 206, an electronic switch 213 and power supply 214, mirror 209, transport mechanism 218, controller 216, sensor 202, analog-to-digital converter (A-D) 230 and processing system 231. System 200 further comprises platen 203, upon which rests a source medium 204 (e.g. a document) containing an image 204a to be captured. Sensor 202 further comprises on optical assembly 210, such as a lens, and a sensing device 212, such as a charge-coupled device ("CCD") or a photomultiplier. Within sensor 202, optical assembly 210 is arranged to focus reflected light from a source medium 204 for detection and capture by charge-coupled device ("CCD") 212 in a manner well known in the art. Processing system 231 is preferably a combination of various hardware and software elements, with the hardware operating upon the programming instructions provided by the software elements in order to implement the features described herein. Of course various combinations of hardware and software can be used, and are contemplated by the present invention. FIG. 2 illustrates the image processor as containing an image processor 233 that is used for image processing and defect corrector 235, which is used for defect correction processing. Both image processor 233 and corrector 235 can be implemented using a combination of processing software and controller 216 or an additional processor, depending upon the processing capabilities of controller 216 and the processing demands of included image and defect processing software.

It should be understood that the system described in FIG. 2 is illustrative and other configurations of hardware elements can be made and be within the spirit and scope of the present invention. For instance, mirrors such as mirror 209 are not necessarily needed, various combinations of different mirrors can be used, more than a single sensor can be used, and different positions of sensors and illuminators are possible. The description provided hereinafter regarding the manner in which defects are capable of being detected should be broadly construed to cover embodiments that allow for such detection according to the present invention to take place.

Image and defect capturing is preferably effectuated as light produced by first and second light sources 208 and 206 illuminates and is reflected from document 204 and by mirror 209, and is captured by sensor 202. Sensor 202, upon receipt of light, outputs image and defect information, which A-D converter 230 converts to digital image and defect data, and which digital data is then processed by image processor 233 and defect corrector 235 respectively.

First and second light sources 208 and 206 are preferably arranged for separate operation such that, during scanning, illumination from first light source 208 is used to capture an image (including defects), while the second light source 206 is used to capture only image 204a defects. For example, when light from first light source 208 illuminates document 204, the light reflected from document 204 and mirror 209, and then received by sensor 202, will contain image information including information on any defects that might be present on the surface of the document 204. When light from the second light source 206 illuminates document 204, the light received by sensor 202 (again passing through platen 203 and reflected by document 204 and mirror 209) will contain information that, as described hereinafter, can be used to identify defects in image 204a. First and second light sources 208 and 206 produce light in accordance with application of power from power supply 214 via the electronic switch 213. Electronic switch 213, which comprises for example, transistors or relays, is regulated by controller 216 in a manner preferably utilized in conventional flatbed scanners for controlling a light source. The type of light that is preferable for first and second light sources 208 and 206 is preferably visible light, which can come from LED's, fluorescent, or other light producing sources, although it should be understood that any other type of light, such as infrared light, can also be used and be within the spirit and scope of the present invention.

Controller 216, in addition to controlling electronic switch 213, is also coupled to transport mechanism 218 via control lines 220 and 222 for sending thereto signals to control the relative positioning of system 200 elements during the preferred separate capturing of image information and defect data, as will be discussed. Controller 216 can further be connected to sensor 202 and A-D converter 230, and can implement processing system 231 as discussed above. Controller 216 can comprise, for example, a programmable microcontroller such as an MC68HC05 made by Motorola.

Transport mechanism 218 preferably responds to control information from controller 216 by relatively aligning system 200 elements for separate capturing of image and defect information. More specifically, a first alignment will preferably provide for conventional image capturing, and a second alignment will preferably provide for defect capturing, as will be discussed hereinafter.

Since the current defect-handling application is a flatbed scanner, preferably transport mechanism 218 effectuates such alignment by moving mirror 209 and sensor 202 typically in a synchronized manner. However, a desirable result of such movement is relative re-positioning of system 200 elements to facilitate the above light path, rather than movement of any particular element or elements. For example, a particular image-capturing device might lack a mirror or operate more preferably through movement of one or more other elements, such as platen 203, source medium 204, sensor 202, LS1 208 and/or LS2 206. The invention further enables the use of a single light source for both image and defect capturing, among other aspects, as will be discussed hereinafter. Therefore, the operation of transport mechanism should be broadly construed to include relative re-positioning of elements such that light is reflected from a source image and received by a sensor in a manner consistent with the teachings herein. The range of mirror movement is preferably such that sensor 202 can sequentially receive light reflected from all portions of document 204 where document 204 is illuminated by light source 208 or light source 206. Mechanisms for moving a document, platen, sensor, mirror or combination of elements, for example, are well known in the art of copiers, printers, scanners, facsimile machines and the like.

Figure 8:
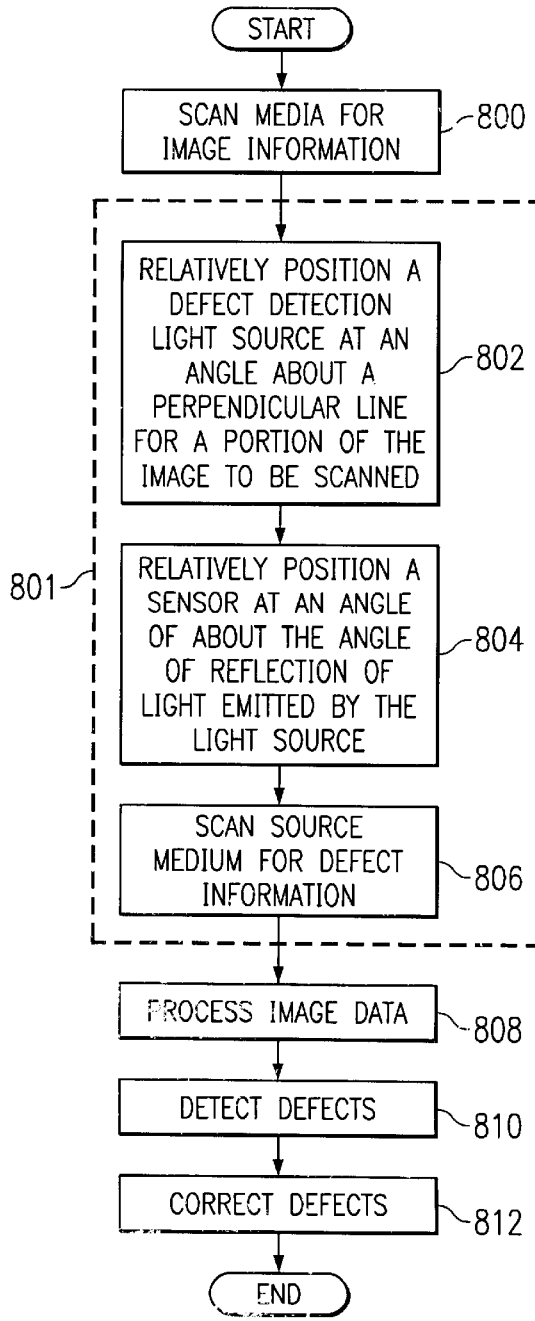
FIG. 8 is a flowchart illustrating a preferred method for capturing defect data and identifying and correcting captured defects according to the invention.

Operationally, controller 216 preferably provides control signals for two separate scan cycles (See also FIG. 8, steps 800 and 801). During an "image scan" cycle, image data (including any defects) is captured, and during a separate "defect scan" cycle only defect data is captured. While a single "full-pass" scan is preferred for expediency, multiple scans can also be used. During a full-pass scan, for example, controller 216 preferably sends first movement control signals 220 and 222 to transport mechanism 218 to move mirror 209 and sensor 202 in a conventional full-pass manner. More specifically, during an image scan cycle, mirror 209 and sensor 202 are moved responsively to first control signals 220 in a first scan direction; then, during a defect scan cycle, mirror 209 and sensor 202 are moved responsively to second control signals 222 in preferably an opposite direction. (A reverse scan cycle order can also be utilized.) Using half-pass scans, for example, controller 216 preferably sends movement control signals 220 and 222 respectively to transport mechanism 218 to move mirror 209 in a first scan direction during an image scan, and then to return mirror 209 to substantially its initial position; next, during a defect scan cycle, controller again sends movement control signal 220 to transport mechanism 218 to move mirror 209 in substantially the first scan direction. (Once again, a reverse scan cycle order can be utilized.)

A single scan cycle can also be used with multiple light sources to provide both image and defect scan data, for example, by adjusting mirror 209 or adding an additional mirror, one-way mirror and/or sensor, as will become apparent to those skilled in the art.

Concurrently with either full-pass or multiple scanning, controller 216 also preferably provides control signals for effectuating image and defect capturing as discussed. For example, first and second control signals 220 and 222 are preferably sent in conjunction with first and second control signals 224 and 226 to control application of power to first and second light sources 208 and 206 respectively. Controller 216 can also send additional control signals (not shown) such that, consistent with conventional image scanning, light is supplied, a sensor is activated, and sensed light is captured during a given scan cycle. Alternatively, multiple controllers, CPUs, digital signal processors ("DSPs") and/or other data processing elements can also be used, depending on the application. The state of LS1 208 and LS2 206 other than during an image or defect scan cycle can be adjusted according to the constraints of a particular application.

The reflective properties of light that are advantageously used by the present invention will now be described. As previously mentioned, this invention teaches an advantageous arrangement of hardware to record defect data at an angle roughly equal to the angle at which light is directed to an object, i.e. where the angle of reflection roughly equals the angle of incidence. As is well known in optics, at this angle the incident light wave comes into contact with the surface of the object and splits into two light waves, one going upward, the other downward.

The upward wave is reflected from the surface of the object and, at this angle, provides the greatest amount of information about that surface. For example, it shows the greatest difference between the amplitudes of light reflected from defect-free areas of the surface and from defects on the surface. Light reflected from surface defects has a wider diffusion and thus a lower amplitude than light reflected from the surface of the object itself.

The downward wave is transmitted into the object and then reflected upward again. It provides the greatest information about the color of the object and is conventionally used to record image color.

Figure 1:
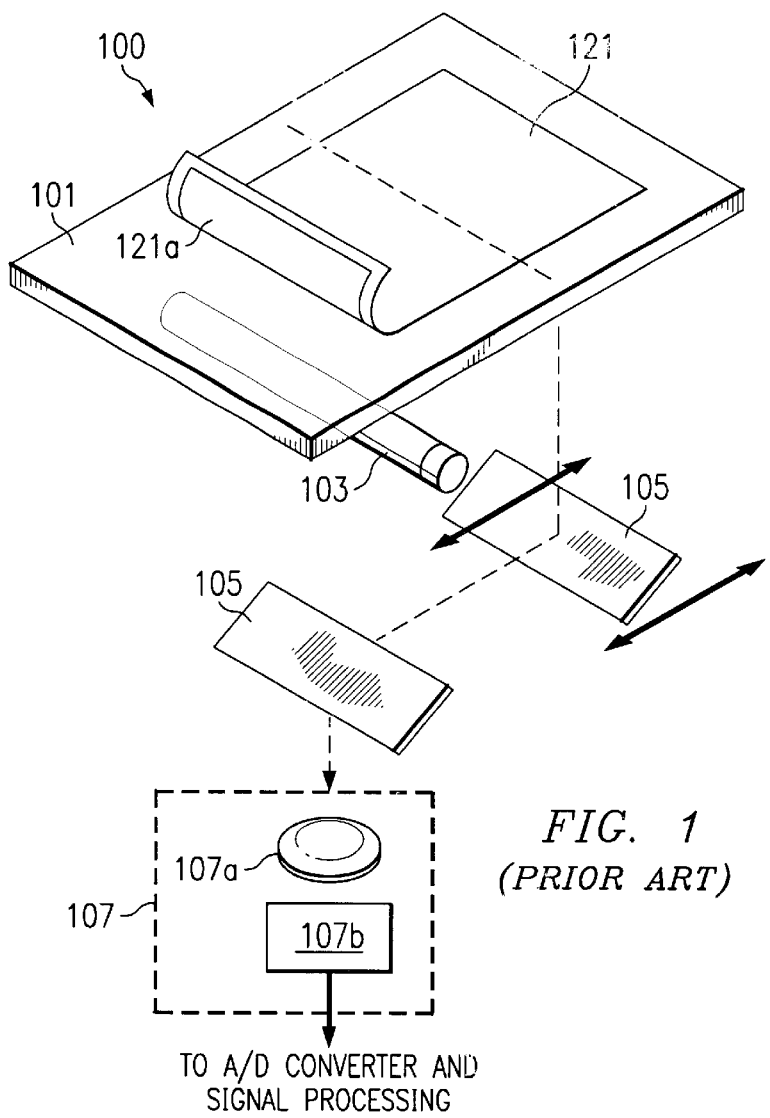
FIG. 1 illustrates a prior-art flatbed scanner.
Figure 3:
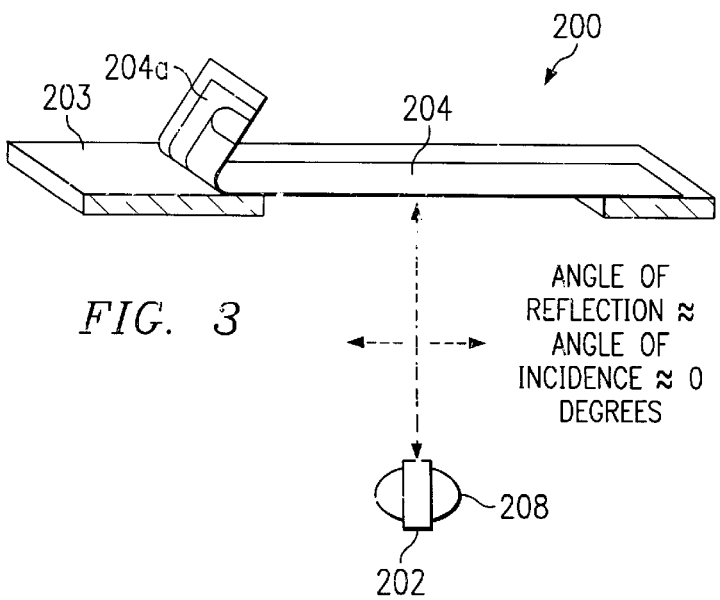
FIG. 3 illustrates how light is preferably provided and reflected during an image scan cycle according to the present invention.

FIG. 3 illustrates how light is preferably provided and reflected during an image scan cycle according to the present invention. As illustrated, during an image scan cycle, light from light source 208 preferably impinges on the surface of document 204 at a 90 degree angle, and after the light is reflected downward as described above, it is reflected back and is then detected by light source 202. Such manner of detection of an image is well known in the art and need not be further described.

Figure 4:
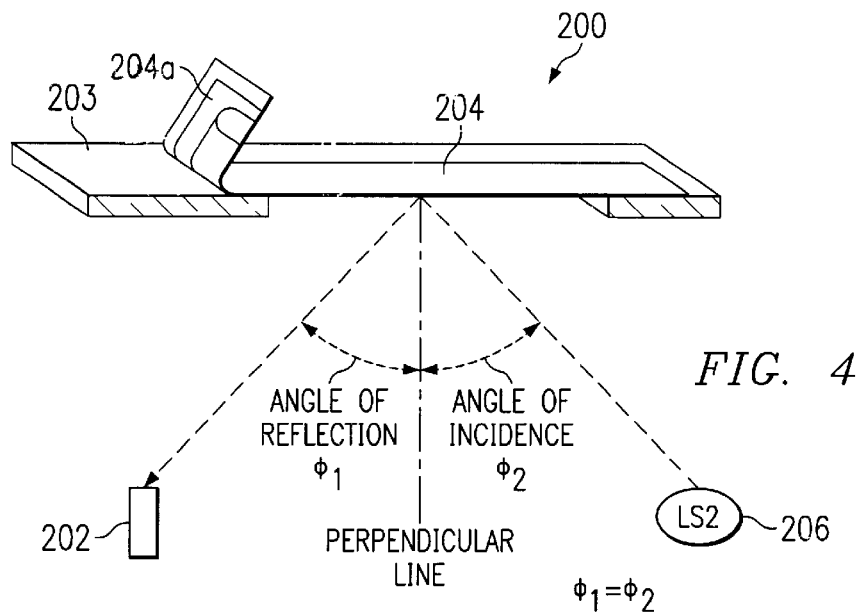
FIG. 4 illustrates how light is preferably provided and reflected during a defect scan cycle according to the present invention.

FIG. 4 illustrates how light is preferably provided and reflected during a defect scan cycle according to the present invention. A preferred flatbed scanner example is shown wherein document 204 containing image 204a is positioned over platen 203. However, only the essential system 200 elements are included in FIG. 4 in order to more clearly depict how relative positioning of the document with respect to sensor 202 and light source 206 during a defect scan cycle provides for more accurate defect detection.

As briefly discussed above, the term "relative positioning" is used to broadly denote that an effort has been made to remain compatible with a common configuration of conventional desktop scanners, wherein available space is limited and a mirror is typically used for folding light. Therefore, during an image scan cycle, mirror 209 (FIG. 2) is preferably aligned with a light source, document and sensor and then moved (while retaining such alignment or "relative positioning") for image capturing. Then, in a similar manner, mirror 209 is preferably re-aligned (and then moved) for capturing defect data during a defect scan cycle, as will now be discussed. In other applications and/or with other image capturing devices and/or device configurations, however, similar image and defect scan cycles might be implemented using these and/or other elements as might be applicable. In such cases, those skilled in the art will understand that similar relative positionings can be achieved through alignment of applicable elements.

As shown in FIG. 4, preferably LS2 206 and sensor 202 are relatively positioned during a defect scan cycle such that a first angle $\phi_1$ at which light emitted by LS2 206 is received by image 204a is about equal to a second angle $\phi_2$ at which light reflected from image 204a is received by sensor 202. Theoretically, the first and second angles are equal, but in practice a slight difference in the angles is more effective because it prevents possible reflections off the surface of the platen 203. The optimum degree of difference in the angles depends on the materials and design of the apparatus, but the difference will typically be less than 20° degrees, and is preferably less than 10°. Further, the range of angles in which the light from light source 206 is incident on the media surface is preferably within the range of 35°–145°, with the range of 45°–135° being most preferred, although light incident at other angles is within the intended scope of the invention. Still furthermore, since the range of 45°–135° includes 90° incident light, it should be further noted that although 90° incident light will work, in practice it is difficult to implement due to the need to have the illuminator and the sensor on the same optical path. Accordingly, in such an implementation, a one way mirror or the like will typically also be required. Thus, due to this constraint, the most preferable ranges of angles at which the light is incident on the document 204 is within the range of 45°–80° and 100°–135°.

Using these relative positionings, sensor 202 will receive the greatest amount of information about the surface of image 204a. In particular, due to this alignment of the sensor 202 and the light source 206, the information that sensor 202 receives will show the greatest difference between the amplitudes, i.e. intensities, of light reflected from the defect-free areas on the surface of image 204a and from any defects on the surface of image 204a.

Figure 5:
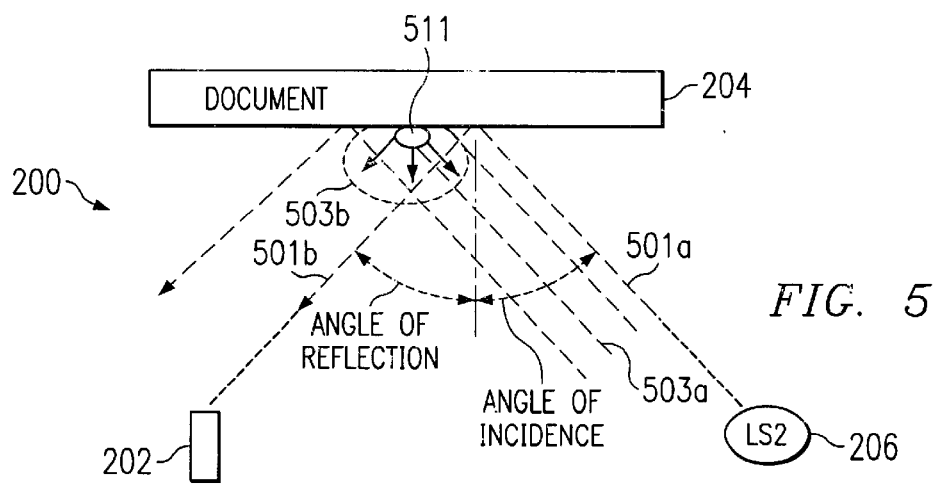
FIG. 5 illustrates how the relative positioning of FIG. 3a provides for capturing the presence or absence of a defect in a region of an image according to the invention.

FIG. 5 illustrates light being reflected from foreign matter or a surface defect, such as a particle of dust between an image and a capturing system (e.g. flatbed scanner 200) or a scratch on the image. As shown, the light that impinges on the surface defect is reflected differently than light reflected from the image's surface where no defect exists. Specifically, foreign matter 511 has been introduced between document 204 (FIG. 2) and light emitted by LS2 206 and received by sensor 202. Light vectors representing how the path of such light is impacted by the presence or absence of an obstruction (such as foreign matter 511) are indicated as arrows. Segments of the arrows extending from LS2 206 or "incident light vectors" are labeled with an "a" subscript and corresponding segments extending to sensor 202 or "reflective light vectors" are labeled with a "b" subscript.

As illustrated, if an incident light vector is received by document 204, then a corresponding reflective light vector will have nearly the full intensity of the incident light vector, at the angle of reflection if a defect does not exist at the portion of the document 204 at which the light vector strikes. (This, of course, assumes that the preferred relative positioning of LS2 206 and sensor 202 has been successful such that little or no absorption occurs due to image details.) For example, vector 501a will be reflected with substantially no intensity loss as vector 501b. Therefore, if vector 501b is captured by sensor 202, sensor 202 will output electrical signals corresponding to a relatively high intensity light. In contrast, incident light vector 503a, when received by foreign matter, such as dust, will be reflected in random directions or "diffused" (as indicated by vectors 503b) due to the irregular shape of the foreign matter. The diffusion will further cause a decrease in light intensity. Therefore, if vector 503b is captured by sensor 202 at the (unobstructed) angle of reflection, sensor 202 will output electrical signals corresponding to a relatively low intensity light. Stated alternatively, using the preferred relative positionings of LS2 206 and sensor 202 during a defect scan cycle, sensor 202 will receive relatively high intensity light where a portion of a source image is scanned and will receive relatively low intensity light where a portion of a defect is scanned. Therefore, during a defect scan cycle, any existing defects will be captured and can then be identified and corrected.

Figure 6:
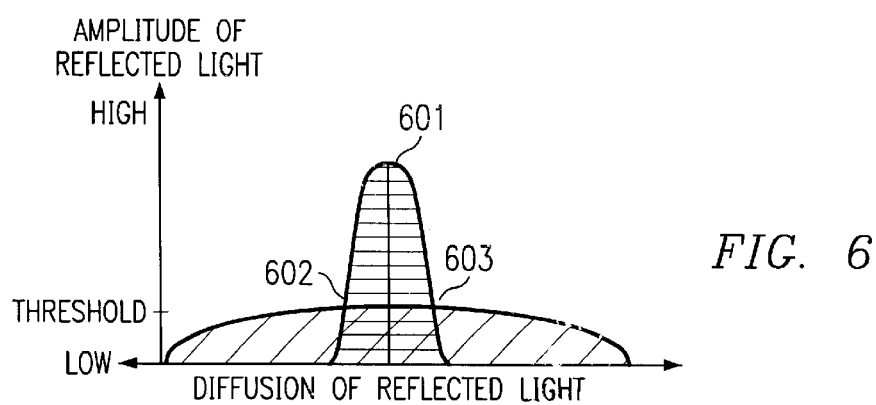
FIG. 6 is a graph illustrating how the relative amplitudes of reflected light produced by the presence or absence of a defect preferably provide for detecting defects according to the invention.

The FIG. 6 graph illustrates the relative amplitude and diffusion of light reflected from an object and from a surface defect on that object, as captured by a system where the angle of incidence roughly equals the angle of reflection. The light reflected from the object has a high amplitude 601 and a narrow pattern of diffusion. The light reflected from a surface defect on the object has a low amplitude 603 and a wide pattern of diffusion. A threshold 602 can be established in between the high amplitude level of the object's reflected light and the low amplitude of the defect's reflected light. For example, an effective threshold can be established at 25% of an object's highest amplitude of reflected light. The system can thus identify as defects any pixels that have an amplitude of reflected light at or below the threshold. Specifically, the software within the defect corrector 235 calculates a threshold value for defects based on a percentage of the maximum amplitude, and subsequently identifies as defects those areas on the object that reflect light with an amplitude at or below the threshold value, as will now be described with respect to FIG. 7.

Figure 7:
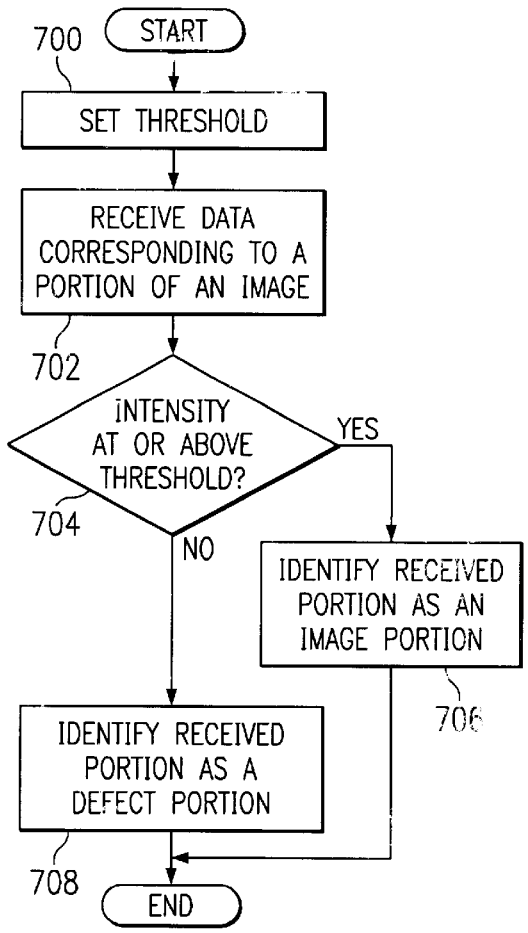
FIG. 7 is a flowchart illustrating a preferred method for detecting defects in captured image data according to the invention.

Given the intensity differentials for image information and defect information already discussed, a preferred method used by defect corrector 235 in FIG. 2 to detect defects in an image will now be discussed by reference to FIG. 7. (As noted previously, image processing is preferably conducted by image processor 233 in a conventional manner.)

As shown, in step 700, a threshold light-intensity value is set. In step 702, image processor 233 (FIG. 2) receives from sensor 202 (via D-A converter 230) data corresponding to a portion of an image (or defect) captured during a defect image cycle. If, in step 704, the light-intensity value of the received data is at or above the threshold set in step 700, then image processor 233 identifies the portion as a portion of the image in step 706. If instead, in step 704, the light-intensity value is below the light-intensity threshold, then, in step 708, image processor 233 identifies the portion as a portion of a defect. Various methods can then be used for defect correction, analysis or other purposes.

It should noted, however, that considerable variation in the above detection method is likely. For example, a static threshold might be where defect detection is performed on a typically similar source media having similar detail characteristics and where the same or a similar light source is used. However, a modifiable threshold might also be used where anticipated conditions are more variable. In addition, automatic modification might also be provided, for example, by capturing color, illumination intensity and/or other characteristics of a sample or actual source image and/or by scanning a source identification label, among other methods. User intervention might also be provided, for example, where a subjective determination is appropriate. Other image-handling criteria might also apply, including but not limited to criteria relating to image capturing, defect detection, photography, graphics and printing, to name a few.

Having explained aspects of the present invention and the basis upon which such aspects operate in accordance with an exemplary apparatus, a following preferred method for detecting and correcting defects will be better understood with reference to FIG. 8.

In step 800, a source medium is scanned for image information. In step 801, the medium is scanned for defects. More specifically, a defect-detection light source is relatively positioned to a portion of the medium to be scanned in step 802. In step 804, a sensor is relatively positioned at an angle of about the angle of reflection of light emitted by the light source and then reflected (unobstructed) from the medium to the sensor. Next, in step 806, the medium is scanned for defects. In step 808, the image data is processed, preferably in a conventional manner, as discussed. In step 810 the defect data is processed to identify any defects. Finally, in step 812, the defects are corrected.

Those skilled in the art will appreciate that the above method is subject to variation consistent with the invention. As discussed, for example, certain of the above steps might be conducted in a different order. Another example is that the image data and/or defect data might be stored, retrieved, transferred, further processed and/or otherwise manipulated as is commonly done with computer-readable data.

Figure 9:
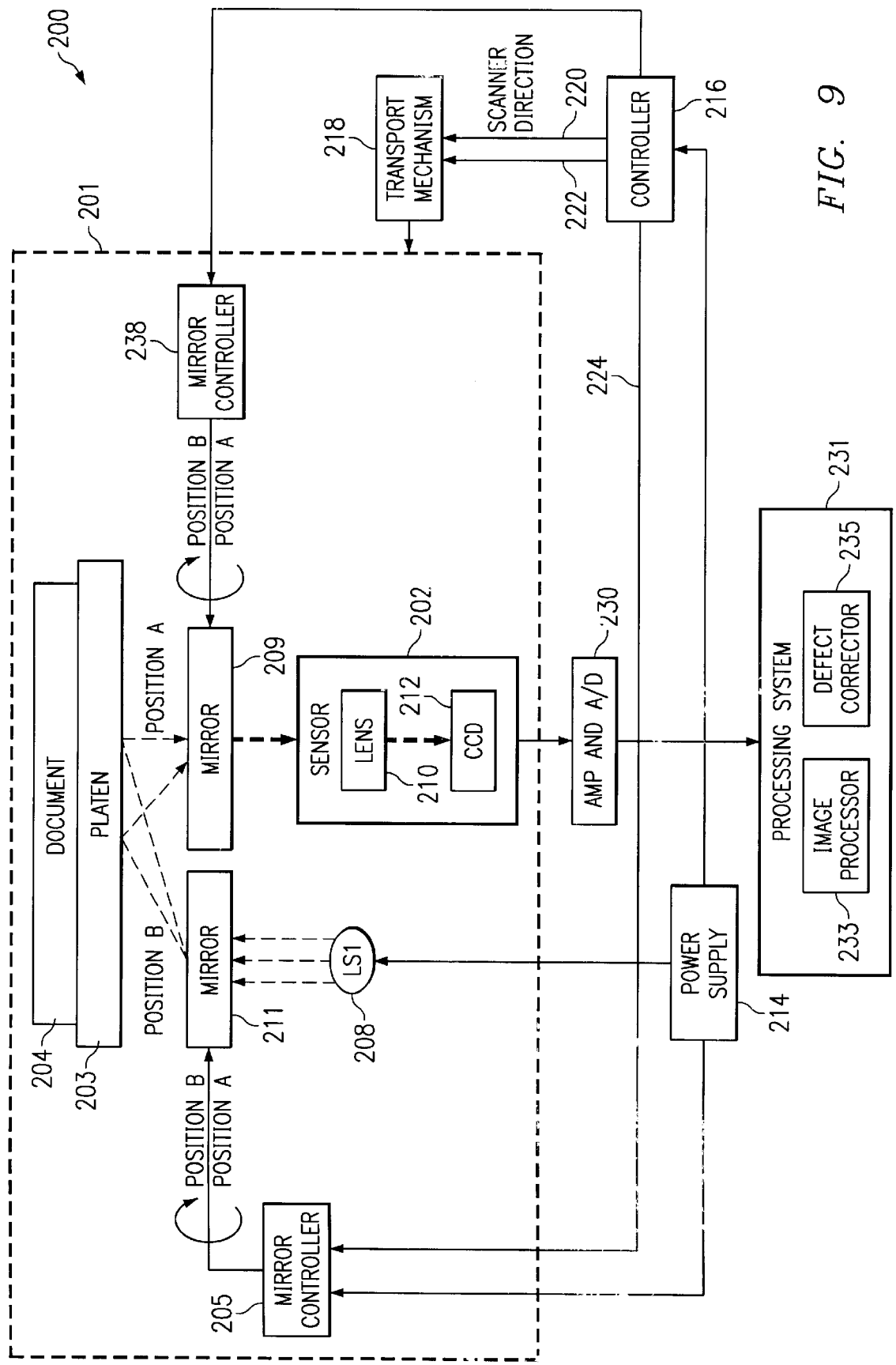
FIG. 9 illustrates a further exemplary flatbed scanner embodiment in which a single light source and/or a single scan cycle is used.

FIG. 9 illustrates another example of an image-capturing system according to the invention. The scanner system of FIG. 9 is essentially the same as the previous embodiment described with reference to FIG. 2, except that LS2 206 (FIG. 2) is removed and a second mirror 211 and two mirror controllers 205 and 238 are provided, such that relative positioning can be achieved using a single light source and during a single scan cycle. Stated alternatively, during one cycle for capturing image data (including defects) consistent with conventional image capturing, mirror 209 is preferably relatively positioned to its position A by mirror controller 238, and mirror 211 to its position A by mirror controller 205. For capturing defect data as discussed above, preferably mirror 209 is relatively positioned to its position B by mirror controller 238 and mirror 211 to its position B by mirror controller 205. Placing both mirrors in their B positions permits creation of an angle where the angle of incidence roughly equals the angle of reflection, allowing the detection of defects.

As discussed, however, a relative positioning of elements consistent with the invention rather than a specific capturing configuration is preferred. Thus, for example, a single light source can also be utilized according to a full or multi-scan without a need for an additional mirror, as should now be apparent to those skilled in the art. One configuration might, for example, re-position mirror 209 during a single cycle. Another configuration might, for example, utilize one-way mirrors to simultaneously provide relative positioning for image capture and defect capture. Other configurations might also be utilized. As discussed, the invention enables numerous devices, device configurations and operational variations (e.g. single versus multiple scans, separate versus concurrent image and defect processing, etc.) depending on the capturing device utilized and/or the specific capturing application.

The invention has been described above with particular reference to application with a reflective medium such as documents. However, it should be understood that the principles of the invention can be extended as well to images and defects captured on transmissive media, including but not limited to film and transparencies.

Figure 10:
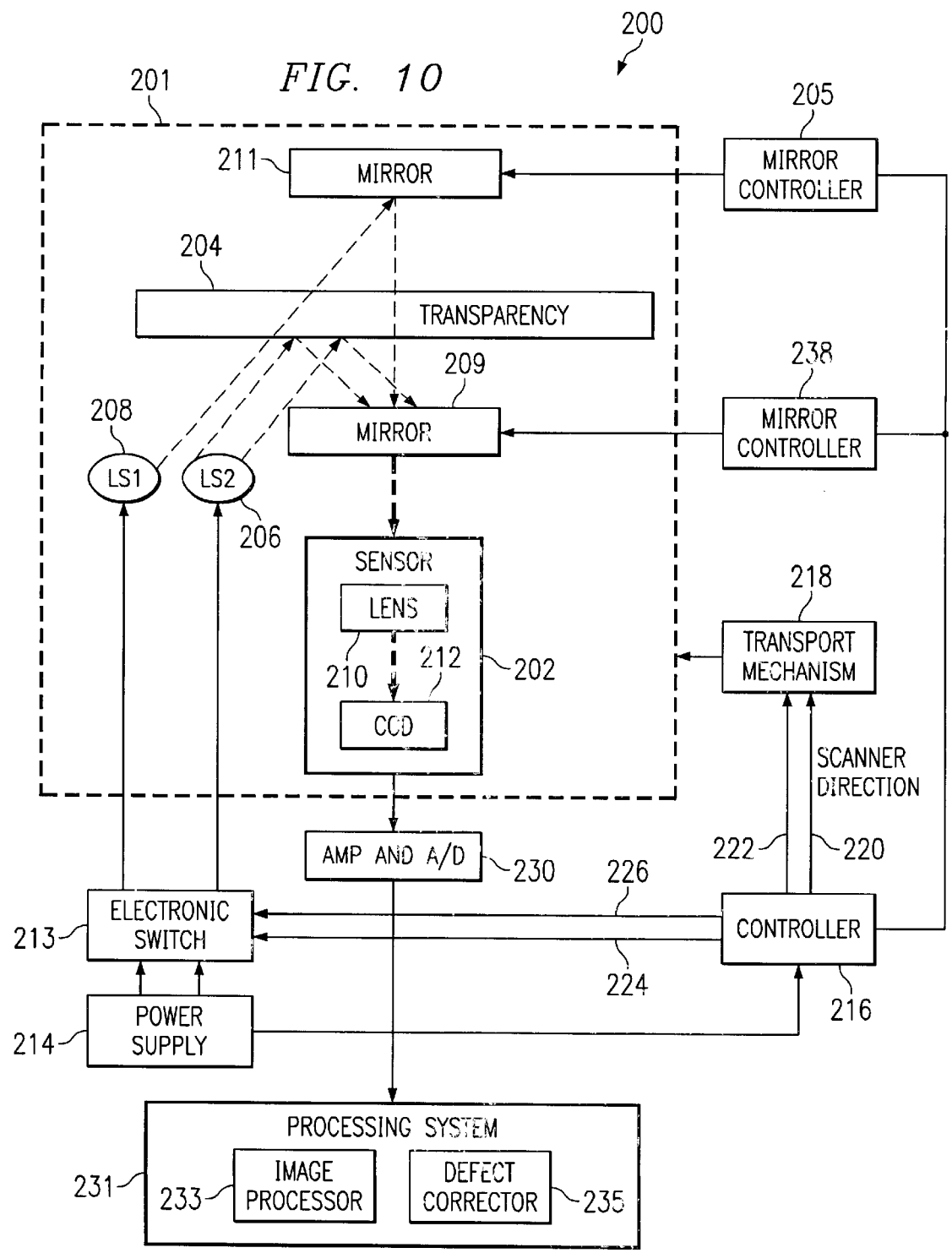
FIG. 10 illustrates a further embodiment useful for capturing defect data in a transmissive medium such as film according to the invention.

FIG. 10 illustrates, for example, a preferred embodiment of the invention for use with images captured in transmissive medium such as film 204, or more specifically a developed color negative film. As shown, the system is essentially the same as the FIG. 2 embodiment except that mirror 211 and mirror controllers 205 and 206 are added. The elements of this system can be arranged so that light from a first light source 208 is transmitted through film 204 and reflected from mirror 211 to mirror 209, which folds it in to sensor 202, to capture image information. Afterwards light from a second light source 206, placed so that the angle of incidence roughly equals the angle of reflection, is reflected from the surface of film 204 to capture defect information. It should be noted, however, that in other applications light might alternatively or additionally be reflected from film, requiring some further modification in accordance with the invention. As discussed, the invention is equally applicable to a variety of applications that might utilize a specific image-capturing device, device configuration and/or operation. For example, single light source and/or scan cycle configurations, among others, are enabled. Such variations, only some of which have been specifically noted, should become apparent to those skilled in the art in light of the foregoing discussion.

Although the present invention has been described in detail with reference to the preferred embodiments thereof, those skilled in the art will appreciate that various substitutions and modifications can be made to the examples described herein while remaining within the spirit and scope of the invention as defined in the appended claims.

We claim:

1. A method of reproducing a portion of an image disposed on a media surface including the steps of:
    illuminating a portion of image with a first light beam transmitted at a first predetermined angle with respect to the media surface;
    detecting the first light beam to obtain image media data;
    illuminating the portion of the image a second light beam transmitted at a second predetermined angle with respect to the media surface;
    detecting the second light beam after the second light beam reflects off of the portion of the image to obtain defect data, wherein the reflected second light that is reflected at a third predetermined angle with respect to the media surface is detected, the difference between the second predetermined angle and the third predetermined angle being about 20 degrees or less; and
    using the image media data and the defect data to reproduce the portion of the image.

2. A method according to claim 1 wherein the difference between the first predetermined angle and the third predetermined angle is about 10 degrees or less.

3. A method according to claim 1 wherein the first light beam is reflected off of the media surface and the step of detecting the first light beam detects the reflected first light beam.

4. A method according to claim 1 wherein the first light beam is transmitted through the media surface and the step of detecting the first light beam that has been transmitted through the media surface.

5. A method according to claim 1 wherein the step of detecting the second light beam includes the steps of:
    focussing the reflected second light beam using an optical assembly to obtain a focussed reflected second light beam; and
    detecting the focussed reflected second light beam.

6. A method according to claim 1 further comprising the step of steering the second light beam reflected off of the media surface using a mirror prior to the step of detecting the second light beam.

7. A method according to claim 1 wherein the step of detecting the second light beam detects a portion of the reflected second light beam that corresponds to an area of the portion of the image containing the defect as having a lesser intensity than another portion of the detected second light beam that is reflected on another area of the portion of the image that does not contain any defect.

8. A method according to claim 1 wherein the second predetermined angle is within the range of 35°–145°.

9. A method according to claim 8 wherein the second predetermined angle is within the range of 45°–80° and 100°–135°.

10. An apparatus for producing a defect data stream that replicates a defect that exists on a portion of an image disposed on a media surface comprising:
    a second light source for illuminating the portion of the image with a second light beam, the second light beam striking the portion of the image at a time that is different than when the first light source illuminates the portion of the image, and wherein the second light beam is detected in order to obtain image data;
    a first light source for illuminating a portion of image with a light beam, the light beam striking the portion of the image at a first predetermined angle with respect to the media surface; and
    a detector for detecting the light beam after the light beam reflects off of the portion of the image to obtain defect data, wherein the detector detects reflected light that is reflected off of the portion of the image at a second predetermined angle with respect to the media surface is detected, the difference between the first predetermined angle and the second predetermined angle being about 20 degrees or less.

11. An apparatus according to claim 10 further including at least one optical device for allowing the detector to detect both the first light beam and the second light beam, wherein the second light beam is transmitted through the media surface.

12. An apparatus according to claim 11 wherein the optical device is a mirror.

13. An apparatus according to claim 10 wherein the detector includes an optical assembly and a charge coupled device array.

14. An apparatus according to claim 10, wherein the first light beam illuminates the image at a time that is different than when the second light beam illuminates the image.

15. An apparatus according to claim 10, wherein at least one light source comprises a mirror.

* * * * *